united States Patent [19]

Luft et al.

[11] Patent Number: 4,959,498
[45] Date of Patent: Sep. 25, 1990

[54] PROCESS FOR THE PREPARATION OF MONOCARBOXYLIC ANHYDRIDES

[76] Inventors: Gerhard Luft, Ludwigstrasse 141a, Mühltal; Peter Trabold, Ahornweg 19a, Dieburg, both of Fed. Rep. of Germany

[21] Appl. No.: 326,607

[22] Filed: Mar. 17, 1989

[30] Foreign Application Priority Data

Apr. 2, 1988 [DE] Fed. Rep. of Germany ....... 3811343

[51] Int. Cl.$^5$ ............................................. C07C 51/54
[52] U.S. Cl. .................................................. 562/891
[58] Field of Search ......................................... 562/891

[56] References Cited

U.S. PATENT DOCUMENTS 4,115,444  9/1978  Rizkalla ............................... 260/549
4,252,741  2/1981  Porcelli et al. ....................... 260/549
4,776,987  10/1988 Luft et al. ............................ 260/549

Primary Examiner—Paul J. Killos
Attorney, Agent, or Firm—Connolly & Hutz

[57] ABSTRACT

The process for the preparation of monocarboxylic anhydrides of the general formula $(RCO)_2O$ is carried out by reacting a carboxylic ester or a dialkyl ether of the general formula RCOOR or ROR, in which R in each case denotes the same alkyl radical having 1 to 4 carbon atoms, with carbon monoxide in the gas phase in the presence of a supported catalyst. The reaction takes place by means of bromine or iodine or compounds thereof as reaction promoter. The support material in the catalyst supports a noble metal chelate compound which is formed by a noble metal compound from group VIII of the periodic table and a chelating agent containing organonitrogen, organophosphorus, organoarsenic, organosulfur or mercapto groups and substituted in its basic structure with alkyl, aryl or aralkyl groups. The reaction is carried out at temperatures from 130° to 400° C. and pressures from 1 to 150 bar.

15 Claims, No Drawings

PROCESS FOR THE PREPARATION OF MONOCARBOXYLIC ANHYDRIDES

The invention relates to a process for the preparation of monocarboxylic anhydrides of the general formula $(RCO)_2O$ by reaction of a carboxylic ester or dialkyl ether of the general formula RCOOR or ROR, in which R in each case denotes the same alkyl radical having 1 to 4 carbon atoms, with carbon monoxide in the gas phase in the presence of iodine or bromine or compounds thereof as reaction promoter and also in the presence of a supported catalyst at temperatures from 130° to 400° C. and pressures of 1–150 bar, the support material in the supported catalyst supporting a noble metal chelate compound which is formed from a noble metal compound from group VIII of the periodic table and a chelating agent containing organonitrogen, organophosphorus, organoarsenic, organosulfur or mercapto groups.

Such a process operating in the gas phase using a supported catalyst has already been disclosed in German Offenlegungsschrift No. 3,511,050, which avoids the disadvantages associated with liquid phase processes, for example the difficult removal and recycling of suspended and partially dissolved catalyst and possibly promoter.

The object of the present invention is to modify the chelating agent in such a manner that service life (duration of activity) and selectivity of the supported catalyst in combination with the same support material are significantly improved.

In detail, according to the process of the invention,

1. The chelating agent is substituted in its basic structure by alkyl, aryl or aralkyl groups and has one of the following structural formulae:

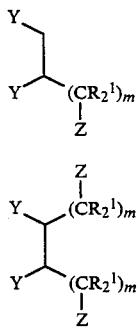

in which Y is $-NR_2^2$, a nitrogen-containing aryl radical, $-PR_2^2$, $-AsR_2^2$, $-SR^2$ or $-SH$;

Z is $-H$, aryl, phenyl (which may be ortho-, meta- or para-substituted)

$R^1$ is $-H$, $C_1$ to $C_3$-alkyl;

$R^2$ is $C_1$ to $C_6$-alkyl, $C_5$ or $C_6$-cycloalkyl, $-C_6H_5$ or $C_6H_5CH_2-$, which may be substituted by halogen, methoxy, ethoxy or $C_1$ to $C_3$-alkyl groups;

m is 2–6, preferably 2–4.

Furthermore, according to the process of the invention, alternatively and preferably 2. The support material in the supported catalyst additionally supports a base metal chelate compound which is formed by a base metal compound from subgroup 6 or 8 of the periodic table of the elements and a chelating agent according to 1.

3. The supported catalyst additionally contains base metal compounds from main groups 1 to 3 or subgroups 4 to 6 or 8 of the periodic table of the elements as promoters.

4. The supported catalyst contains an inorganic oxidic support material or an activated carbon support.

5. The supported catalyst altogether contains 0.01 to 50 % by weight, preferably 0.1 to 20 % by weight, of chelate compounds and, if desired, base metal compounds.

6. The supported catalyst is used in a particle size from 1 to 20 mm.

Suitable catalyst supports are preferably inorganic oxides, such as, for example, $SiO_2$, $Al_2O_3$, $MgO$, $TiO_2$, $La_2O_3$, $ZrO_2$, zeolite, clay, NiO, $Cr_2O_3$, $WO_3$ or the corresponding mixed oxides, but also activated carbon which have BET surface areas of 1–1000 $m^2/g$, preferably 30–400 $m^2/g$.

As according to German Offenlegungsschrift No. 3,511,050, the promoters of main groups 5 or 6 in the chelating agents or chelating ligands used according to the invention are chemically bound. They themselves form a functional group which chelates the noble metal compounds from group VIII and, if present, base metal compounds from subgroups 6 or 8. It is advantageous that the promoters from main groups 5 or 6 of the periodic table of the elements necessary for increasing the activity and selectivity of the supported catalysts form a functional group Y in the chelating agents and are thus fixed, as a result of which removal and recycling of these, for example, organonitrogen or organophosphorus promoters is unnecessary.

The process of the invention for the preparation of monocarboxylic anhydrides exhibits higher selectivities and, particularly on long-term use, higher service lives of the supported catalyst compared to the process of German Offenlegungsschrift No. 3,511,050.

A further advantage of the process of the invention resides in the fact that the modified noble metal chelate compounds and, if present, base metal chelate compounds which are applied to the support material have even higher melting points (240°–270° C.) than the complexes described in German Offenlegungsschrift No. 3,511,050, which leads to a higher thermal stability of the catalysts or to an increase in the range of application by 20° to 50° C.

The process of the invention serves in particular for the preparation of acetic anhydride from metal acetate or dimethyl ether in the presence of methyl iodide or methyl bromide as reaction promoter. Other reaction promoters which can be used are HI, HBr or in general RI or RBr, in which R represents an alkyl radical having 1–4 carbon atoms.

The support materials have already been mentioned; suitable mixed oxides are, for example, $Cr_2O_3$-$Al_2O_3$, $WO_3$-$Al_2O_3$, $MgO$-$Al_2O_3$, $SiO_2$-$Al_2O_3$ or $ZrO_2$-$Al_2O_3$. The supported catalyst preferably contains 0.05 to 5 % by weight of noble metal.

For example, the following compounds can be used during the preparation of the supported catalyst as noble metal compounds:

Rhodium:

$RhCl_3$, $RhCl_3.3H_2O$, $RhBr_3$, $RhI_3$, $Rh(NO_3)_3$, $Rh_2(CO)_4Cl_2$, $Rh_2(CO)_4Br_2$, $Rh(CO)_4I_2$, $[P(C_6H_5)_3]_3$

RhCl, [P(C₆H₅)₃]₂Rh(CO)Cl, Rh₆(CO)₁₆, Rh₄(CO)₁₂, Rh₂(O₂CCH₃)₄, [RhCl(C₈H₁₂)]₂;

Iridium:

IrCl₃, [Ir(CO)₃Cl]₂, Ir[P(C₆H₅)₃]₂(CO)Cl, Ir₄(CO)₁₂, [IrCl(C₈H₁₂)]₂, Cl(CO)₂Irpyr (pyr=C₆H₅N);

Palladium:

PdCl₂, PdBr₂, PdI₂, (CH₃CO₂)₂Pd[P(C₆H₅)₃]₂, PdCl₂[P(C₆H₅)₃]₂, Pd(O₂CCH₃)₂, PdCl₂(C₈H₁₂), (C₆H₅CN)₂PdCl₂;

Ruthenium:

RuCl₃, Ru₃(CO)₁₂, RuCl₂[P(C₆H₅)₃]₃, RuCl₂(CO)₂[P(C₆H₅)₃]₂, [RuCl₂(CO)₃]₂.

Suitable base metal compounds from subgroups 6 or 8, in particular Cr, Ni, but also W, Fe, Co, which also react with the chelating agents, are for example:

Chromium:

Cr(CO)₆, CrCl₃, C₇H₈Cr(CO)₃.

Nickel:

Ni(CO)₄, [P(C₆H₅)₃]₂Ni(CO)₂, NiCl₂, Ni(C₈H₁₂)₂.

Base metal compounds from main groups 1 to 3 or subgroups 4 to 6 or 8 of the periodic table, preferably those of Li, Na, Mg, Ca, Al, Ti, Zr, V, Cr, W, Fe, Co, Ni, which can be used, are, for example, hydroxides, carbonates, carbonyls, hydrides, halides and other salts. These compounds of base metals can be applied additionally, for example as solution, to the catalyst support by impregnation.

RhCl, $[P(C_6H_5)_3]_2Rh(CO)Cl$, $Rh_6(CO)_{16}$, $Rh_4(CO)_{12}$, $Rh_2(O_2CCH_3)_4$, $[RhCl(C_8H_{12})]_2$;

Iridium:

$IrCl_3$, $[Ir(CO)_3Cl]_2$, $Ir[P(C_6H_5)_3]_2(CO)Cl$, $Ir_4(CO)_{12}$, $[IrCl(C_8H_{12})]_2$, $Cl(CO)_2Irpyr$ (pyr=$C_6H_5N$);

Palladium:

$PdCl_2$, $PdBr_2$, $PdI_2$, $(CH_3CO_2)_2Pd[P(C_6H_5)_3]_2$, $PdCl_2[P(C_6H_5)_3]_2$, $Pd(O_2CCH_3)_2$, $PdCl_2(C_8H_{12})$, $(C_6H_5CN)_2PdCl_2$;

Ruthenium:

$RuCl_3$, $Ru_3(CO)_{12}$, $RuCl_2[P(C_6H_5)_3]_3$, $RuCl_2(CO)_2[P(C_6H_5)_3]_2$, $[RuCl_2(CO)_3]_2$.

Suitable base metal compounds from subgroups 6 or 8, in particular Cr, Ni, but also W, Fe, Co, which also react with the chelating agents, are for example:

Chromium:

$Cr(CO)_6$, $CrCl_3$, $C_7H_8Cr(CO)_3$.

Nickel:

$Ni(CO)_4$, $[P(C_6H_5)_3]_2Ni(CO)_2$, $NiCl_2$, $Ni(C_8H_{12})_2$.

Base metal compounds from main groups 1 to 3 or subgroups 4 to 6 or 8 of the periodic table, preferably those of Li, Na, Mg, Ca, Al, Ti, Zr, V, Cr, W, Fe, Co, Ni, which can be used, are, for example, hydroxides, carbonates, carbonyls, hydrides, halides and other salts. These compounds of base metals can be applied additionally, for example as solution, to the catalyst support by impregnation.

To prepare the supported catalyst used according to the invention, first the chelator containing the functional groups Y has to be provided. It can be prepared according to or analogously to literature data. In general one of the noble metal compounds mentioned from group VIII and, if present, one of the base metal compounds mentioned from subgroup 6 or 8 are combined as a solution with the chelating agent, thus forming chelate compounds whose melting points are above the temperature of the carbonylation reaction for the preparation of monocarboxylic anhydrides.

This is followed by impregnation of the support material by the dissolved chelate compounds to give the ready-to-use supported catalyst. The solvents for the chelate compounds in which the support material is suspended can be polar or unpolar, for example dichloromethane, chloroform, methanol, benzene, toluene or xylene. All other details regarding syntheses are evident from the description of the catalyst preparation.

The relative amounts of carboxylic ester or dialkyl ether and iodine (compound) or bromine (compound) in the reaction zone can vary within wide limits. In general the amount of carboxylic ester and/or dialkyl ether is 1 to 500 mol, preferably 1 to 100 mol, per mole of iodine (compound) or bromine (compound). The temperature of the reaction zone is selected such that the reaction mixture is present as a gas irrespective of the degree of conversion. The temperature is preferably selected between 150° and 250° C. The preferred pressure is between 5 and 30 bar.

The residence time of the reaction mixture over the solid supported catalyst is 1 to 1000 s, preferably 1 to 180 s. The reaction can be carried out in a flow tube arranged vertically and filled with supported catalyst or even in a stirred or shaken autoclave containing the supported catalyst. The carbonylation is in general carried out under anhydrous conditions, although small amounts of water, such as are present in commercially available starting materials, are acceptable but should not exceed 1 mole %, calculated for the starting materials. Neither is the carbonylation impaired by small amounts of methanol in the starting materials. Hydrogen, which may be present in small amounts in commercially available carbon monoxide, does not interfere either.

The reaction mixture which leaves the carbonylation zone is gaseous and contains carbon monoxide, methyl iodide, acetic anhydride, unconverted methyl acetate or dimethyl ether and possibly very small amounts of acetic acid. The gaseous reaction mixture is cooled, acetic anhydride and, if present, acetic acid are condensed and the uncondensed substances such as CO, methyl iodide, methyl acetate or dimethyl ether are returned to the reaction zone. The converted portions of ester or ether and also CO are continuously replaced. The simple removal of the anhydrides by cooling of the discharged reaction mixture and recycling of the uncondensable gases constitutes, as in the process of German Offenlegungsschrift No. 3,511,050, a significant advantage, since this can be done without any complicated separation procedures. The supported catalyst is not contaminated and remains in the reaction zone, which considerably simplifies the entire course of the process.

Examples

Experiments using a stirred autoclave

A stirred autoclave, capacity 0.25 liter, made of stainless steel (Hastelloy C) and equipped with the necessary inlets and outlets and containing a rotatable catalyst basket is used. The carboxylic esters or dialkyl ethers are reacted as gases in the presence of the moving solid supported catalyst with CO gas. The supported catalyst is present in the rotatable catalyst basket, which at the same time effects the thorough mixing of the gases.

The autoclave is charged with 2.5 ml of a liquid mixture of 20 parts by volume of methyl iodide and 80 parts by volume of ester or ether, and the mixture is heated to the reaction temperature. The carbonylation is initiated by injection of carbon monoxide. The CO pressure is kept constant by regular additional injection. The details of the experimental procedures can be seen from the examples.

Example 1

2 ml (1.86 g) of methyl acetate, 0.5 ml (1.14 g) of methyl iodide and 6.46 g of catalyst No. 1 are reacted in the autoclave with carbon monoxide at a CO pressure of 15 bar and at 180° C. After a reaction time of 1 hour, a catalyst output of 23 g of $Ac_2O/g_{Rh} \times h$ at a selectivity of 98% is obtained.

Example 2

2 ml (1.86 g) of methyl acetate, 0.5 ml (1.14 g) of methyl iodide and 6.77 g of catalyst No. 2 are reacted in the autoclave with carbon monoxide at a CO pressure of 15 bar and at 180° C. After a reaction time of 1 hour, a catalyst output of 22 g of $Ac_2O/g_{Rh} \times h$ at a selectivity of 98% is obtained.

Example 3

2 ml (1.86 g) of methyl acetate, 0.5 ml (1.14 g) of methyl iodide and 7.98 g of catalyst No. 3 are reacted in the autoclave with carbon monoxide at a CO pressure of 15 bar and 180° C. After a reaction time of 1 hour, a catalyst output of 28 g of $Ac_2O/g_{RH} \times h$ at a selectivity of 96% is obtained.

Example 4

2 ml (1.86 g) of methyl acetate, 0.5 ml (1.14 g) of methyl iodide and 5.04 g of catalyst No. 4 are reacted in the autoclave with carbon monoxide at a CO pressure of 15 bar and at 180° C. After a reaction time of 1 hour, a catalyst output of 44 g of $Ac_2O/g_{RH} \times h$ at a selectivity of 97% is obtained.

Example 5

A steel tube, 20 mm in diameter and 400 mm in length, is arranged vertically as a flow tube and charged with 52.8 g of catalyst No. 1. At a pressure of 12 bar and a temperature of 180° C., 8 Nl of CO(Nl=liters measured at 1.013 bar and 0° C.) and also an evaporated mixture (12.9 ml of liquid) consisting of methyl iodide and methyl acetate (molar ratio 1:4) are passed through the flow tube per hour.

The reaction mixture which leaves the tube is analyzed on-line by gas chromatography. A space/time yield of 15.4 g of $Ac_2/g_{Rh} \times h$ at a selectivity of 99% is obtained. Under these reaction conditions, the carbonylation was carried out for 280 hours, during which time the supported catalyst used did not show any loss in activity.

Example 6

A steel tube, 20 mm in diameter and 400 mm in length, is arranged vertically as a flow tube and charged with 51.0 g of catalyst No. 2. At a pressure of 12 bar and a temperature of 180° C., 8 Nl of CO(Nl=liters measured at 1.013 bar and 0° C.) and also an evaporated mixture (13.5 ml of liquid) consisting of methyl iodide and methyl acetate (molar ratio 1:4) are passed through the flow tube per hour.

The reaction mixture which leaves the tube is analyzed on line by gas chromatography. A space/time yield of 14.3 g of $Ac_2/g_{RH} \times h$ at a selectivity of 99% is obtained. Under these reaction conditions, the carbonylation was carried out for 280 hours, during which time the supported catalyst used did not show any loss in activity.

Description of the preparation of the catalyst

In all cases, the catalyst support was previously dried for the purpose of activation at 200° C. and 0.1 mbar for 10 hours. After application of the metal component, the catalysts were heated to boiling with chlorotrimethylsilane for 8 hours and then dried at 0.1 mbar and 100° C. All syntheses were carried out in an argon atmosphere in the absence of atmospheric oxygen and water. All solvents used had previously been dried over a molecular sieve 4 A, or if possible, using benzophenone sodium.

The symbol "$\theta$" used in the formula below stands for the phenyl radical ($C_6H_5$).

Catalyst No. 1

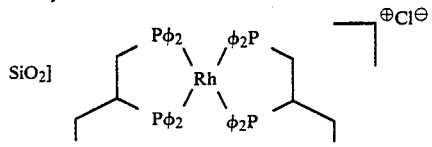

65.4 g of activated silicon dioxide pellets ⅛"×⅛" (95% of $SiO_2$) having an internal surface area according to a BET of 68 m²/g and a pore volume of 0.43 ml/g were treated with 150 ml of a solution from 629 mg of complex 4 in dichloromethane: The yellow suspension was heated at the reflux temperature for 15 hours, during which the solvent became completely colorless. After evaporation of dichloromethane under reduced pressure, the catalyst was dried at 0.1 mbar and 150° C. for 6 hours.

Characterization: Yellow pellets
Rh content: 0.1% by weight

Synthetic route of rhodium complex 4

1,2-Dichlorobutane (2):

2 can be obtained by reaction of 1-butene (1) with chlorine at 0° C. in dichloromethane in almost quantitative yield.

1,2-Bis(diphenylphosphino)butane (3):

3 is synthesized by reaction of a two-fold molar amount of sodium diphenylphosphide in dioxane with 2 dissolved in tetrahydrofuran, at room temperature [analogously to 1,2-bis(diphenylphosphino)ethane; see K. Issleib and D. W. Müller, Chem. Ber. 92, 3175 (1959)]. Yield 78%.

[1,2-Bis(diphenylphosphino)butane]rhodium(I) chloride (4):

A solution of 4 mmol of 3 in benzene is added dropwise with stirring to a solution of 1 mmol of dichlorotetracarbonyldirhodium in benzene, in the course of which complex 4 precipitates in analytical purity.

Yield 94%. cf. Synthesis of [1,2-bis(diphenylphosphino)-ethane]rhodium(I) chloride: A. Sacco et al., J. Chem. Soc. (London), 3274 (1964).

Catalyst No. 2

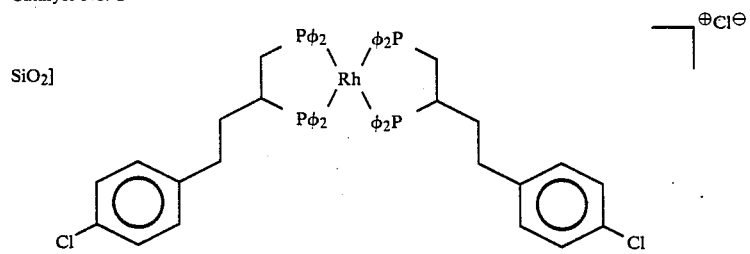

68.3 g of activated silicon dioxide pellets ⅛"×⅛" (95% of $SiO_2$) having an internal surface area according to BET of 68 m²/g and a pore volume of 0.43 ml/g were treated with 150 ml of a solution from 723 mg of complex 8 in dichloromethane. The yellow suspension was heated at the reflux temperature for 15 hours, during which the solvent became completely colorless. After evaporation of dichloromethane under reduced pressure, the catalyst was dried at 0.1 mbar and 150° C. for 6 hours.

Characterization: Yellow pellets
Rh content: 0.09% by weight

Synthetic route of rhodium complex 8

1,2-Dichloro-4-(4-chlorophenyl)butane (6):

6 can be synthesized by reaction of 4-(4-chlorophenyl)butene (5) with chlorine at 0° C. in dichloromethane.
Yield 93%.

1,2-Bis(diphenylphosphino)-4-(4-chlorophenyl)butane (7):

7 is synthesized by reaction of a two-fold molar amount of sodium diphenylphosphide in dioxane with 6 dissolved in tetrahydrofuran, at room temperature in a yield of 82 % [analogously to 1,2-bis(diphenylphosphino)ethane; see K. Issleib and D.-W. Müller, Chem. Ber. 92, 3175 (1959)].

[1,2-Bis(diphenylphosphino)-4-(4-chlorophenyl)-butane]rhodium(I) chloride (8):

A solution of 4 mmol of 7 in benzene is added dropwise with stirring to a solution of 1 mmol of dichlorotetracarbonyldirhodium in benzene, in the course of which complex 8 precipitates in analytical purity. Yield 96%. cf. Synthesis of [1,2-bis(diphenylphosphino)ethane]rhodium(I) chloride; A. Sacco et al., J. Chem. Soc. (London), 3274 (1964).

Catalyst No. 3 pressure, the catalyst was dried at 0.1 mbar and 150° C. for 6 hours.

Characterization: Yellow pellets
Rh content: 0.08% by weight

Synthetic route of rhodium complex 12

1,6-Diphenylhex-3-ene (9):

Alkene 9 was synthesized by reaction of dihydrocinnamic aldehyde with tri-phenylpropyltriphenylphosphonium bromide in a yield of 64% [Wittig reaction; see Organikum, 15th edition, p. 494, VEB Deutscher Verlag der Wissenschaften, Berlin 1977].

3,4-Dichloro-1,6-diphenylhexane (10):

10 can be synthesized by reaction of 9 with chlorine at 0° C. in dichloromethane. Yield 96%.

3,4-Bis(diphenylphosphino)-1,6-diphenylhexane (11):

11 is synthesized by reaction of a two-fold molar amount of sodium diphenylphosphide in dioxane with 10, dissolved in tetrahydrofuran, at room temperature in a yield of 74% [analogously to 1,2-bis(phenylphosphino)ethane; see K. Issleib and D.-W. Müller, Chem. Ber. 92, 3175 (1969)].

[3,4-Bis(diphenylphosphino)-1,6-diphenylhexane]rhodium(I) chloride (12):

A solution of 4 mmol of 11 in benzene is added dropwise with stirring to a solution of 1 mmol of dichlorotetracarbonyldirhodium in benzene, in the course of which complex 12 precipitates in analytical purity. Yield 97%. cf. Synthesis of [1,2-bis(diphenylphosphino)ethane]rhodium(I) chloride; A. Sacco et al., J. Chem. Soc. (London), 3274 (1964).

Catalyst No. 4

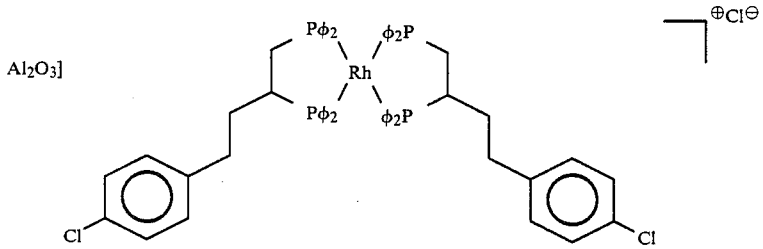

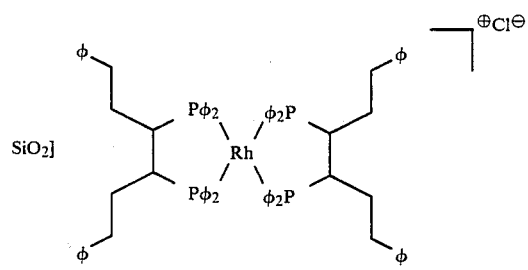

12.8 g of activated silicon dioxide pellets ⅛"×⅛" (95% of SiO$_2$) having an internal surface area according to BET of 68 m$^2$/g and a pore volume of 0.43 ml/g were treated with 50 ml of a solution from 134.6 mg of complex 12 in dichloromethane. The yellow suspension was heated at the reflux temperature for 15 hours, during which the solvent became completely colorless. After evaporation of dichloromethane under reduced 10.0 g of activated alumina beads (99% of Al$_2$O$_3$) having a diameter of 3 mm, an internal surface area according to a BET of 125 m$^2$/g and a pore volume of 0.9 ml/g were treated with 50 ml of a solution from 117.6 mg of rhodium complex 8 in dichloromethane. The yellow suspension was heated at the reflux temperature for 15 hours, during the course of which the solvent became completely colorless. After evaporation of dichloromethane under reduced pressure the catalyst was dried at 0.1 mbar and 150° C. for 6 hours.

Characterization: Yellow beads
Rh content: 0.1 % by weight

We claim:

1. In a process for the preparation of monocarboxylic anhydrides of the formula (RCO)$_2$O by reaction of a carboxylic ester or dialkyl ether of the formula RCOOR or ROR, in which R in each case denotes the same alkyl radical having 1 to 4 carbon atoms, with carbon monoxide in the gas phase in the presence of iodine or bromine or compounds containing iodine or bromine at temperatures ranging from 130° to 400° C. and pressures of 1–150 bar, the improvement which comprises using a supported catalyst having a support material of inorganic oxides, mixed oxides, or activated carbon, supporting a noble metal chelate compound and optionally a base metal chelate compound, the noble metal chelate compound comprising a noble metal compound from group VIII of the periodic table and a chelating agent having organonitrogen, organophosphorus, organoarsenic, organosulfur or mercapto groups, wherein the chelating agent is substituted in its basic structure by alkyl or aralkyl groups and has one of the following structural formulae:

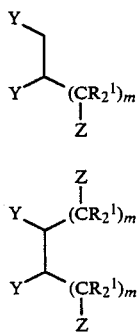
(a)

in which Y is —NR$_2^2$, a nitrogen-containing aryl radical, —PR$_2^2$, —AsR$_2^2$, —SR$^2$ or —SH;

Z is H, aryl, phenyl,

R$^1$ is —H, C$_1$ to C$_3$-alkyl;

R$^2$ is C$_1$ to C$_6$-alkyl, C$_5$ or C$_6$-cycloalkyl, —C$_6$H$_5$ or C$_6$H$_5$CH$_2$—;

m is 2–6.

2. The process as claimed in claim 1, wherein the base metal chelate compound comprises a base metal compound from subgroup 6 or 8 of the periodic table of the elements and a chelating agent as claimed in claim 16.

3. The process as claimed in claim 1, wherein the supported catalyst contains a base metal compound from main groups 1 to 3 or subgroups 4 to 6 or 8 of the periodic table of the elements.

4. The process as claimed in claim 1, wherein the supported catalyst contains an inorganic oxidic support material or an activated carbon which have BET surface areas of 1–1000 m$^2$/g.

5. The process as claimed in claim 1, wherein the supported catalyst altogether contains 0.01 to 50% by weight of chelate compounds and optionally base metal compounds.

6. The process as claimed in claim 1, wherein the supported catalyst is used in a particle size of 1 to 20 mm.

7. The process as claimed in claim 1, wherein substituent Z denotes ortho-, meta- or para-substituted phenyl.

8. The process as claimed in claim 1, wherein substituents R$^2$ are in turn substituted by halogen-, methoxy-, ethoxy or C$_1$ to C$_3$-alkyl groups.

9. The process as claimed in claim 1, wherein m is 2–4.

10. The process as claimed in claim 1, wherein said support material is SiO$_2$, Al$_2$O$_3$, MgO, TiO$_2$, La$_2$O$_3$, ZrO$_3$, zeolite, clay, NiO, Cr$_2$O$_3$, WO$_3$ or the corresponding mixed oxides, or activated carbon which have BET surface areas of 30–400 m$^2$/g.

11. The process as claimed in claim 1, wherein said noble metal chelate compound and optionally said base metal chelate compound have melting points ranging from 240°–270° C.

12. The process as claimed in claim 1, wherein said mixed oxide is Cr$_2$O$_3$—Al$_2$O$_3$, WO$_3$—Al$_2$O$_3$, MgO—Al$_2$O$_3$, SiO$_2$—Al$_2$O$_3$ or ZrO$_2$—Al$_2$O$_3$.

13. The process as claimed in claim 1, wherein said supported catalyst contains 0.05 to 5% by weight of noble metal.

14. The process as claimed in claim 3, wherein said base metal compound is a hydroxide, carbonate, carbonyl, hydride, halide or salt of Li, Na, Mg, Ca, Al, Ti, Zr, V, Cr, W, Fe, Co, or Ni.

15. The process as claimed in claim 1 wherein said temperature ranges from 150° to 250° C., and said pressure ranges from 5 to 30 bar.

* * * * *

UNITED STATES PATENT AND TRADEMARK OFFICE
CERTIFICATE OF CORRECTION

PATENT NO. : 4,959,498

DATED : SEPTEMBER 25, 1990

INVENTOR(S) : LUFT ET AL.

It is certified that error appears in the above-identified patent and that said Letters Patent is hereby corrected as shown below:

On the title page, item (73) Assignee, should read

--Hoechst Aktiengesellschaft, Frankfurt/Main 80, Germany--.

Signed and Sealed this

Twenty-second Day of February, 1994

Attest:

BRUCE LEHMAN

*Attesting Officer*        *Commissioner of Patents and Trademarks*